US008232261B2

(12) United States Patent
Schwarz

(10) Patent No.: US 8,232,261 B2
(45) Date of Patent: Jul. 31, 2012

(54) METHOD OF MINIMIZING HERBICIDAL INJURY

(75) Inventor: Michael R. Schwarz, Raleigh, NC (US)

(73) Assignee: Bayer CropScience LP, Research Triangle Park, NC (US)

( * ) Notice: Subject to any disclaimer, the term of this patent is extended or adjusted under 35 U.S.C. 154(b) by 440 days.

(21) Appl. No.: 10/623,402

(22) Filed: Jul. 18, 2003

(65) Prior Publication Data
US 2005/0014646 A1    Jan. 20, 2005

(51) Int. Cl.
*A01N 57/00* (2006.01)
(52) U.S. Cl. ......... 514/105; 514/106; 514/107; 514/108
(58) Field of Classification Search .................. 504/105, 504/106, 107, 108
See application file for complete search history.

(56) References Cited

U.S. PATENT DOCUMENTS

| | | | |
|---|---|---|---|
| 4,468,246 A | 8/1984 | Pallos | 71/100 |
| 4,523,947 A * | 6/1985 | Szczepanski et al. | 504/105 |
| 4,531,002 A | 7/1985 | Harris | 544/54 |
| 4,590,272 A | 5/1986 | Shiokawa et al. | 544/335 |
| 4,606,862 A | 8/1986 | Harris | 260/402.5 |
| 4,647,570 A | 3/1987 | Shiokawa et al. | 514/341 |
| 4,678,795 A | 7/1987 | Shiokawa et al. | 514/341 |
| 4,680,294 A | 7/1987 | Shiokawa et al. | 514/256 |
| 4,687,838 A | 8/1987 | Mumcu et al. | 528/496 |
| 4,687,845 A | 8/1987 | Hollowood et al. | 544/54 |
| 4,742,060 A | 5/1988 | Shiokawa et al. | 514/252 |
| 4,774,247 A | 9/1988 | Shiokawa et al. | 514/256 |
| 4,803,277 A | 2/1989 | Shiokawa et al. | 514/332 |
| 4,806,553 A | 2/1989 | Shiokawa et al. | 514/332 |
| 4,812,454 A | 3/1989 | Shiokawa et al. | 514/256 |
| 4,812,571 A | 3/1989 | Shiokawa et al. | 546/296 |
| 4,845,106 A | 7/1989 | Shiokawa et al. | 514/342 |
| 4,849,432 A | 7/1989 | Shiokawa et al. | 514/341 |
| 4,882,344 A | 11/1989 | Shiokawa et al. | 514/342 |
| 4,914,113 A | 4/1990 | Shiokawa et al. | 514/333 |
| 4,918,086 A | 4/1990 | Gsell | 514/351 |
| 4,918,088 A | 4/1990 | Gsell | 514/357 |
| 4,948,798 A | 8/1990 | Gsell | 514/275 |
| 4,963,572 A | 10/1990 | Gsell | 514/357 |
| 4,963,574 A | 10/1990 | Bachmann et al. | 514/357 |
| 4,988,712 A | 1/1991 | Shiokawa et al. | 514/340 |
| 5,001,138 A | 3/1991 | Shiokawa et al. | 514/342 |
| 5,032,589 A | 7/1991 | Shiokawa et al. | 514/245 |
| 5,034,404 A | 7/1991 | Uneme et al. | 514/365 |
| 5,034,524 A | 7/1991 | Shiokawa et al. | 544/124 |
| 5,039,686 A | 8/1991 | Davies et al. | 514/341 |
| 5,049,571 A | 9/1991 | Gsell | 514/345 |
| 5,051,434 A | 9/1991 | Kozo et al. | 514/357 |
| 5,063,236 A | 11/1991 | Gsell | 514/318 |
| 5,066,808 A | 11/1991 | Shiokawa et al. | 514/231.5 |
| 5,084,467 A | 1/1992 | Shiokawa et al. | 514/357 |
| 5,166,164 A | 11/1992 | Nanjo et al. | 514/357 |
| 5,192,778 A | 3/1993 | Kodaka et al. | 514/341 |
| 5,204,359 A | 4/1993 | Shiokawa et al. | 514/332 |
| 5,204,360 A | 4/1993 | Shiokawa et al. | 514/342 |
| 5,238,949 A | 8/1993 | Shiokawa et al. | 514/327 |
| 5,256,679 A | 10/1993 | Minamida et al. | 514/357 |
| 5,264,584 A | 11/1993 | Kodaka et al. | 548/332.5 |
| 5,280,123 A | 1/1994 | Nanjo et al. | 548/111 |
| 5,298,507 A | 3/1994 | Shiokawa et al. | 514/256 |
| 5,384,324 A | 1/1995 | Shiokawa et al. | 514/365 |
| 5,405,961 A | 4/1995 | Nanjo et al. | 544/243 |
| 5,428,032 A | 6/1995 | Shiokawa et al. | 514/226.8 |
| 5,461,167 A | 10/1995 | Shiokawa et al. | 548/202 |
| 5,580,889 A | 12/1996 | Shiokawa et al. | 514/343 |
| 5,696,256 A | 12/1997 | Kando et al. | 540/463 |
| 5,719,146 A | 2/1998 | Shiokawa et al. | 514/229.2 |
| RE35,811 E | 5/1998 | Shiokawa et al. | 514/357 |
| 5,750,704 A | 5/1998 | Shiokawa et al. | 546/275.1 |
| 5,852,012 A | 12/1998 | Maienfisch et al. | 514/229.2 |
| 5,876,739 A * | 3/1999 | Turnblad et al. | 424/408 |
| 6,022,871 A | 2/2000 | Maienfisch et al. | 514/229.2 |
| 6,022,967 A | 2/2000 | Shiokawa et al. | 544/298 |
| 6,187,773 B1 | 2/2001 | Wu et al. | 514/245 |
| 6,232,309 B1 | 5/2001 | Shiokawa et al. | 514/222.5 |
| 6,297,374 B1 | 10/2001 | Shiokawa et al. | 544/55 |
| 6,344,453 B1 | 2/2002 | Shiokawa et al. | 514/223.8 |
| 6,376,487 B1 | 4/2002 | Maienfisch et al. | 514/229.2 |
| 6,551,962 B1 | 4/2003 | Pershing et al. | 504/100 |
| 6,586,365 B2 | 7/2003 | Asrar et al. | 504/100 |
| 6,593,273 B2 | 7/2003 | Asrar et al. | 504/100 |
| 6,627,753 B1 | 9/2003 | Maienfisch et al. | 544/67 |
| 2001/0046994 A1 | 11/2001 | Wu et al. | 514/241 |
| 2002/0115564 A1 | 8/2002 | Asrar et al. | 504/100 |
| 2002/0115565 A1 | 8/2002 | Arar et al. | 504/100 |
| 2002/0142916 A1 | 10/2002 | Asrar et al. | 504/100 |

(Continued)

FOREIGN PATENT DOCUMENTS
CA    2 382 615    4/2001

(Continued)

OTHER PUBLICATIONS

Machine Translation of JP 05-139921 to Suzuki et al, published Jun. 8, 1993.*
English Translation of JP 3-261704 to Koichi Suzuki, published Nov. 21, 1991.*
Human translation of JP 05-139921.*
The Pesticide Handbook, 12th edition, (month unavailable) 2000, pp. 1243-1250, C.D.S. Tomlin,ed., British Crop Protection Council, "Index 5".
Chemical Engineering, Dec. 1967, pp. 147-170, J.E. Browning, "Agglomeration".
Weed Control Handbook, 5th edition, (month unavailable) 1968, pp. 101-103, "The Application of Herbicides".
Weed Control: as a Science, (month unavailable) 1961, pp. 81-96, G.C. Klingman, "Surface Active Agents".
Beltwide Cotton Conferences, vol. 2, (month unavailable) 1998, pp. 1177-1180, D. Ames Herbert, Jr., "Evaluation of Thrips Damage of Maturity and Yield of Virginia Cotton".
Arthropod Management Tests, vol. 20, (month unavailable) 1995, pp. 209-211, J.R. Reed and C.S. Jackson, "Insecticides with Disyston 15G as Safener for Command Herbicide on Cotton in Mississippi, 1994".

(Continued)

*Primary Examiner* — Renee Claytor
(74) *Attorney, Agent, or Firm* — Raymond J. Harmuth

(57) ABSTRACT

The present invention provides a method of reducing phytotoxicity or plant injury at a crop plant locus caused by a herbicide application at the locus which method includes applying to the crop plant locus a chloronicotinyl insecticide before the herbicide application.

23 Claims, No Drawings

U.S. PATENT DOCUMENTS

| | | | |
|---|---|---|---|
| 2003/0018992 A1 | 1/2003 | Asrar et al. | 800/279 |
| 2003/0033631 A1 | 2/2003 | Asrar et al. | 800/279 |
| 2003/0186813 A1 | 10/2003 | Pershing et al. | 504/117 |
| 2003/0232821 A1 | 12/2003 | Maienfisch et al. | 514/229.2 |

FOREIGN PATENT DOCUMENTS

| | | |
|---|---|---|
| DE | 36 39 877 | 5/1988 |
| DE | 37 12 307 | 10/1988 |
| JP | 62-287764 | 11/1988 |
| JP | 63-307857 | 12/1988 |
| JP | 2-207083 | 8/1990 |
| JP | 3-220176 | 9/1991 |
| JP | 3-255072 | 11/1991 |
| JP | 3-261704 | 11/1991 |
| JP | 3-279359 | 12/1991 |
| JP | 4-9371 | 1/1992 |
| JP | 5-139921 | 6/1993 |
| JP | 05139921 A * | 6/1993 |
| JP | 3-246283 | 11/1999 |
| WO | 91/17659 | 11/1991 |
| WO | WO 0126468 A2 * | 4/2001 |

OTHER PUBLICATIONS

Arthropod Management Tests, 24, (month unavailable) 1999, pp. 204-205, D.E. Bragg, J. Burns and J. Yenish, Antagonism Between Herbicide and Insecticide in Spring Canola, 1998.

Beltwide Cotton Conferences, vol. 2, (month unavailable) 1997, pp. 1171-1176, S.J. Stringer, H.R. Mitchell, "Effect of Furadan/Disulfoton on Cotton Growth and Development".

Proceedings of the Western Society of Weed Science, vol. 53, Papers Presented at the Annual Meeting, Mar. 14-16, 2000, pp. 30-31, P.J. Schneider, J.P. Yenish, D. Bragg John Burns, and "Antagonism of Insecticide Activity in Canola with Low Doses of Sulfonylurea Herbicides".

* cited by examiner

METHOD OF MINIMIZING HERBICIDAL INJURY

BACKGROUND OF THE INVENTION

The present invention relates to a method of minimizing injury to a plant, particularly a crop plant which injury is caused by a herbicide treatment of the locus of the crop plant. The method of the present invention includes applying to the plant locus, an insecticide, which insecticide operates to reduce or eliminate injury to the plant that would have otherwise occured when the plant was subsequently treated with a herbicide.

Neonicotinoids, which may be otherwise called chloronicotinyls or chloronicotinyl insecticides, are generally known in the field of agriculture. Generally, neonicotinoid insecticides are known as agonists or antanogists of the nicotinic acetylcholine receptors of insects. Some neonicotinoids are described as plant growth enhancers in Patent Cooperation Treaty publication No. WO 01/26468.

Herbicidal treatment of plants, particularly crop plants, can significantly increase crop plant yields and improve the heartiness of the crop plant by removing other vegetation competing for food and water. However, as herbicides operate to eliminate or reduce weeds or other unwanted plants in the area of the crop plant, it is sometimes the case that the herbicide being applied to enhance the plants growth and strength, operates to harm or weaken the very crop plant it was intended to help.

Efforts have been made in the art to produce plants that are resistant to herbicides, as for example certain transgenic plants. Efforts have also been made in the art to develop herbicides which are "safened", which generally means that the herbicide is formulated in such a way that it will not hurt the crop plant while still eliminating the weeds surrounding the crop plant.

However, there remains a need in the art for new and improved ways of treating plants, particularly crop plants, with herbicides to enhance their strength, growth and yield, yet not damaging or otherwise injuring the crop plant with the herbicide.

SUMMARY OF THE INVENTION

The present invention provides a method of reducing phytotoxicity or plant injury at a plant locus, preferably a crop plant locus caused by a herbicide application at the locus which method includes applying to the plant locus a chloronicotinyl insecticide before the herbicide application.

DETAILED DESCRIPTION OF THE INVENTION

Although the scope of the present invention is not limited to crop plants, crop plants known as moncotyledons are generally preferred crop plants which are to be protected by the present invention.

The application of herbicide to the crop plant locus may be as the skilled artisan may desire. Generally either post-emergent or pre-emergent methods of application are used. By the term "pre-emergent" is meant that the herbicide is applied before a green plant has emerged from the ground. A pre-emergent herbicide application may take place at the time of planting of the seed, or before or after planting. By the term "post-emergent" is meant the herbicide is applied to the foliage and ground after the plant has emerged from the ground. In the case of monocotylodons, the application of herbicide can occur over a broad range of above-ground growth stages, but is generally applied between the 2 and 5-leaf stage.

Agonists or antagonists of the nicotinic acetylcholine receptors of insects are known, for example, from European Offenlegungsschriften Nos. 580 553, 464 830, 428 941, 425 978, 386 565, 383 091, 375 907, 364 844, 315 826, 259 738, 254 859, 235 725, 212 600, 192 060, 163 855, 154 178, 136 636, 303 570, 302 833, 306 696, 189 972, 455 000, 135 956, 471 372, 302 389; German Offenlegungsschriften Nos. 3 639 877, 3 712 307; Japanese Offenlegungsschriften Nos. 03 220 176, 02 207 083, 63 307 857, 63 287 764, 03 246 283, 04 9371, 03 279 359, 03 255 072; U.S. Pat. Nos. 5,034,524, 4,948,798, 4,918,086, 5,039,686, 5,034,404; PCT Applications No WO 91/17 659, 91/4965; French Application No. 2 611 114; Brazilian Application No. 88 03 621.

The compounds described in these publications and their preparation are expressly incorporated herein by way of reference.

These compounds are preferably represented by the general formula (I)

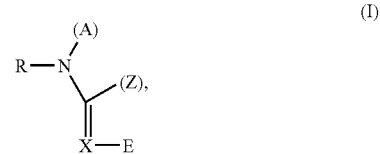

in which
  R represents hydrogen, optionally substituted radicals from the group acyl, alkyl, aryl, aralkyl, heteroaryl or heteroarylalkyl;
  A represents a monofunctional group from the series hydrogen, acyl, alkyl, aryl, or represents a bifunctional group which is linked to the radical Z;
  E represents an electron-withdrawing radical;
  X represents the radicals —CH= or =N—, it being possible for the radical —CH= instead of an H-atom to be linked to the radical Z;
  Z represents a monofunctional group from the series alkyl, —O—R, —S—R,

or represents a bifunctional group which is linked to the radical A or to the radical X

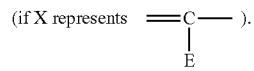

Particularly preferred compounds of the formula (I) are those in which the radicals have the following meaning:
  R represents hydrogen and represents optionally substituted radicals from the series acyl, alkyl, aryl, aralkyl, heteroaryl, heteroarylalkyl.
    Acyl radicals which may be mentioned are formyl, alkylcarbonyl, arylcarbonyl, alkylsulfonyl, arylsulfonyl, (alkyl)-(aryl)-phosphoryl, which may in turn be substituted.

As alkyl there may be mentioned $C_{1-10}$-alkyl, especially $C_{1-4}$-alkyl, specifically methyl, ethyl, i-propyl, sec- or; t-butyl, which may in turn be substituted.

As aryl there may be mentioned phenyl, naphthyl, especially phenyl.

As aralkyl there may be mentioned phenylmethyl, phenethyl.

As heteroaryl there may be mentioned heteroaryl having up to 10 ring atoms and N, O, S especially N as heteroatoms. Specifically there may be mentioned thienyl, furyl, thiazolyl, imidazolyl, pyridyl, benzothiazolyl, As heteroarylalkyl there may be mentioned heteroarylmethyl, heteroarylethyl having up to 6 ring atoms and N, O, S, especially N as heteroatoms.

Substituents which may be listed by way of example and preference are: alkyl having preferably 1 to 4, in particular 1 or 2 carbon atoms, such as methyl, ethyl, n- and i-propyl and n-, i- and t-butyl; alkoxy having preferably 1 to 4, in particular 1 or 2 carbon atoms, such as methoxy, ethoxy, n- and i-propyloxy and n-, i- and t-butyloxy; alkylthio having preferably 1 to 4, in particular 1 or 2 carbon atoms, such as methylthio, ethylthio, n- and i-propylthio and n-, i- and t-butylthio; halogenoalkyl having preferably 1 to 4, in particular 1 or 2 carbon atoms and preferably 1 to 5, in particular 1 to 3 halogen atoms, the halogen atoms being identical or different and being preferably fluorine, chlorine or bromine, especially fluorine, such as trifluoromethyl; hydroxyl; halogen, preferably fluorine, chlorine, bromine and iodine, especially fluorine, chlorine and bromine cyano; nitro; amino monoalkyl- and dialkylamino having preferably 1 to 4, in particular 1 or 2 carbon atoms per alkyl group, such as methylamino, methyl-ethyl-amino, n- and i-propylamino and methyl-n-butylamino; carboxyl; carbalkoxy having preferably 2 to 4, in particular 2 or 3 carbon atoms, such as carbomethoxy and carboethoxy; sulfo (—$SO_3H$); alkylsulfonyl having preferably 1 to 4, in particular 1 or 2 carbon atoms, such as methyl sulfonyl and ethylsulfonyl; arylsulfonyl having preferably 6 or 10 aryl carbon atoms, such as phenylsulfonyl, and also heteroarylamino and heteroarylalkylamino such as chloropyridylamino and chloropyridylmethylamino.

A particularly preferably represents hydrogen and optionally substituted radicals from the series acyl, alkyl, aryl, which preferably have the meanings given for R. A additionally represents a bifunctional group. There may be mentioned optionally substituted alkylene having 1-4, in particular 1-2 C atoms, substituents which may be mentioned being the substituents listed earlier above, and it being possible for the alkylene groups to be interrupted by heteroatoms from the series N, O, S.

A and Z may, together with the atoms to which they are attached, form a saturated or unsaturated heterocyclic ring. The heterocyclic ring can contain a further 1 or 2 identical or different heteroatoms and/or heterogroups. Heteroatoms are preferably oxygen, sulfur or nitrogen, and hetero-groups are preferably N-alkyl, where the alkyl in the N-alkyl group preferably contains 1 to 4, in particular 1 or 2 carbon atoms. As alkyl there may be mentioned methyl, ethyl, n- and i-propyl and n-, i- and t-butyl. The heterocyclic ring contains 5 to 7, preferably 5 or 6 ring members.

Examples of the heterocyclic ring which may be mentioned are imidazolidine, pyrrolidine, piperidine, piperazine, hexamethyleneimine, hexahydro-1,3,5-triazine, hexahydrooxodiazine, morpholine, each of which may optionally be substituted preferably by methyl.

E represents an electron-withdrawing radical, in which context particular mention may be made of $NO_2$, CN, halogenoalkylcarbonyl such as 1,5-halogeno-$C_{1-4}$-carbonyl especially $COCF_3$.

X represents —CH= or —N=

Z represents optionally substituted radicals alkyl, —OR, —SR, —NRR, where R and the substituents preferably have the meaning given above.

Z can form, apart from the abovementioned ring, and together with the atom to which it is attached and with the radical

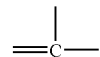

instead of X, a saturated or unsaturated heterocyclic ring. The heterocyclic ring can contain a further 1 or 2 identical or different heteroatoms and/or heterogroups. The heteroatoms are preferably oxygen, sulfur or nitrogen, and the hetero-groups N-alkyl, in which case the alkyl or N-alkyl group preferably contains 1 to 4, in particular 1 or 2 carbon atoms. As alkyl there may be mentioned methyl, ethyl, n- and i-propyl and n-, i- and t-butyl. The heterocyclic ring contains 5 to 7, preferably 5 or 6 ring members.

Examples of the heterocyclic ring which may be mentioned are pyrrolidine, piperidine, piperazine, hexamethyleneimine, morpholine and N-methylpiperazine.

As compounds which may be used with very particular preference in accordance with the invention, mention may be made of compounds of the general formulae (II), (III) and (IV):

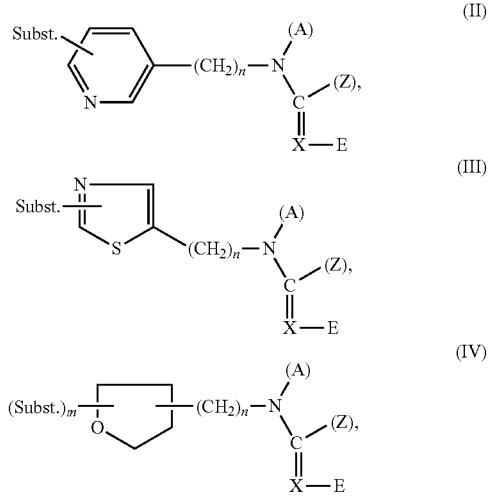

in which
n represents 1 or 2,
m represents 0, 1 or 2,
Subst. represents one of the above-listed substituents, especially halogen, very particularly chlorine,
A, Z, X and E each have the meanings given above.

Specifically, the following compounds may be mentioned:
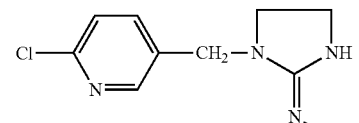
imidacloprid
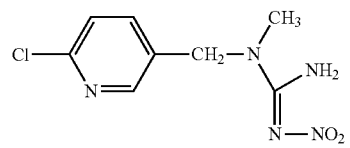
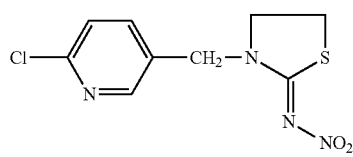
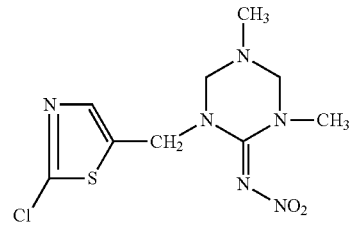
AKD 1022
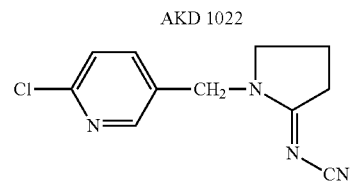
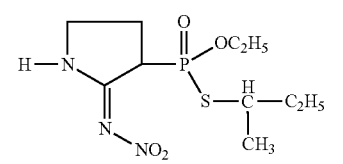
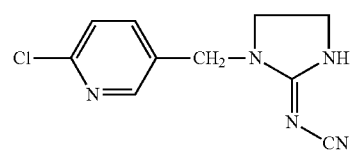
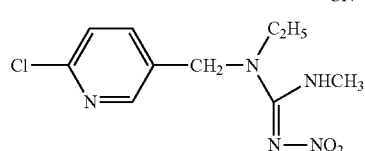
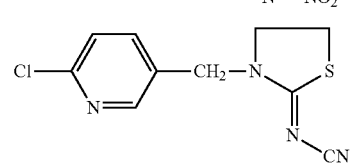
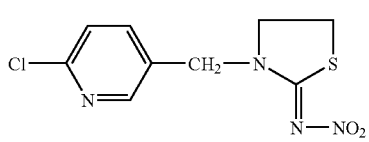
-continued
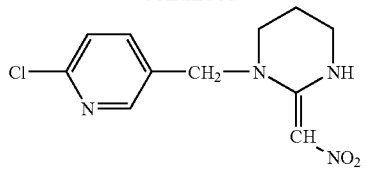
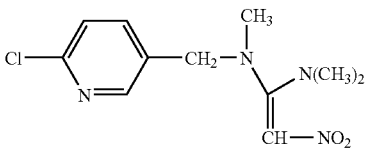
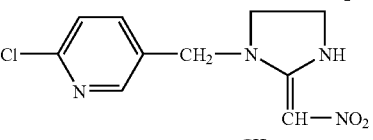
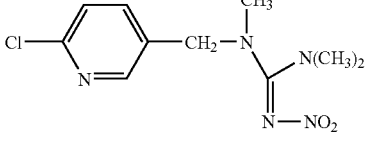
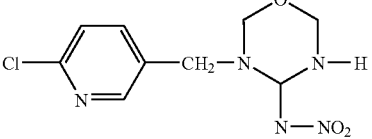
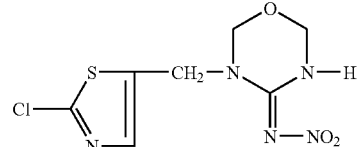
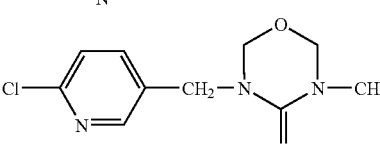
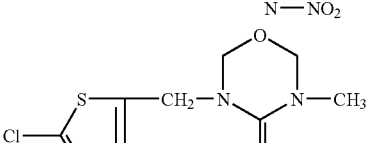
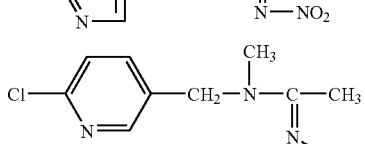
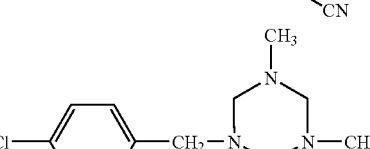
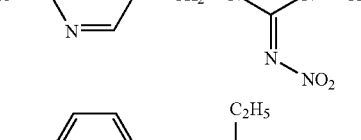

-continued
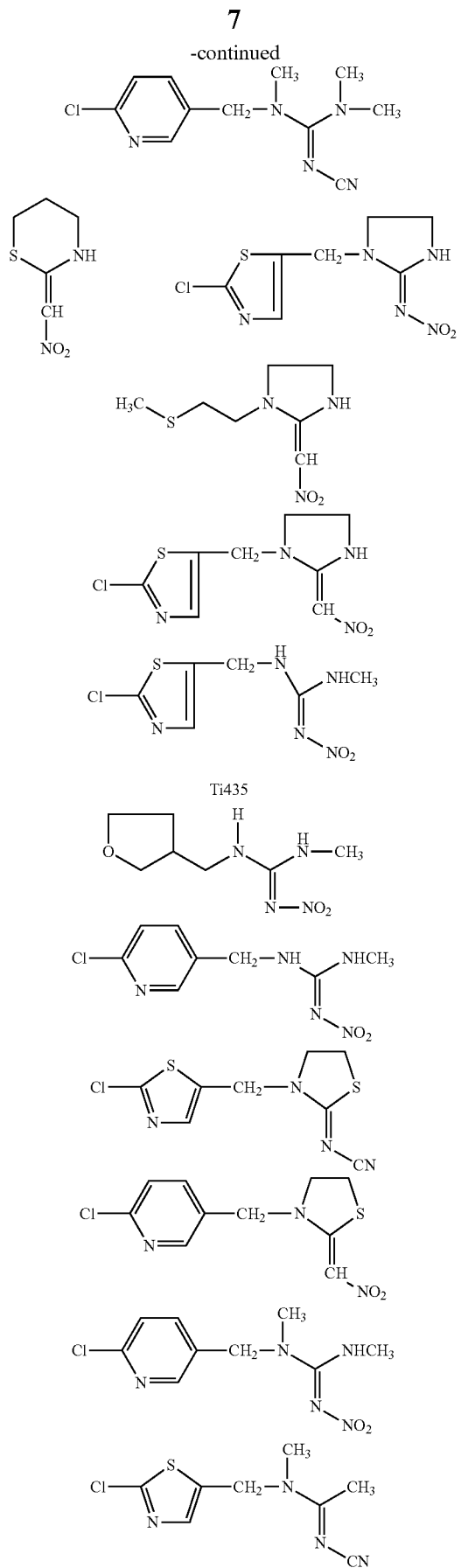
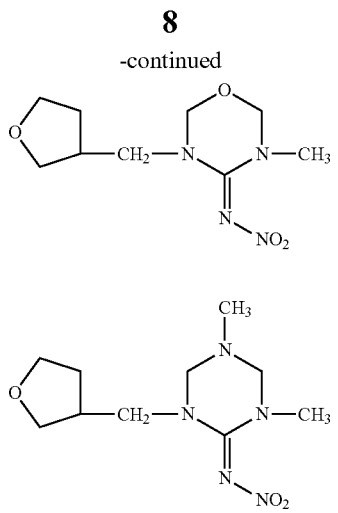
Particular emphasis is given to the compounds
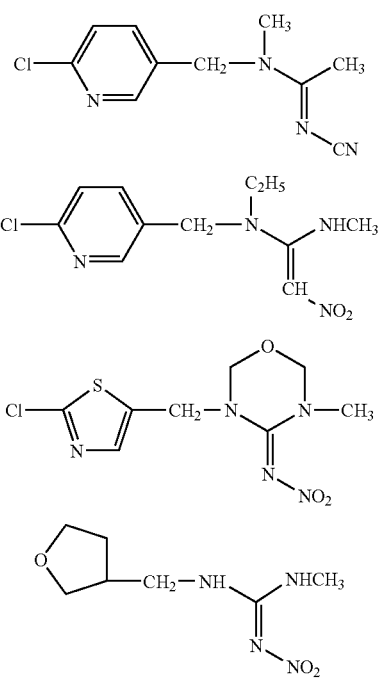
Furthermore, particular emphasis is given to the compounds
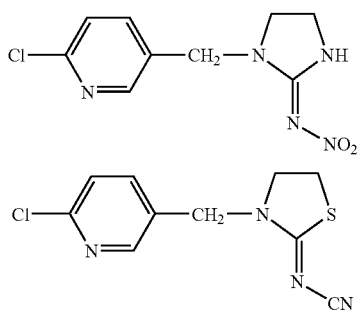

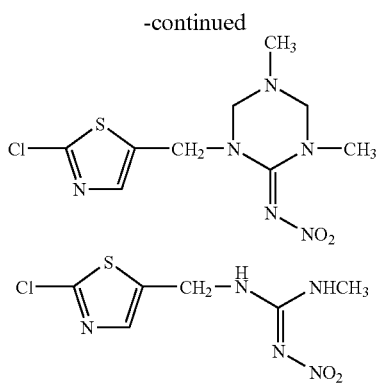

Of the herbicides that may be applied, the following classes are generally noted: chloroacetamides; imidazolinones; oxyacetamides; sulfonylureas; triazines; triketones or the isoxazoles. Such classes are listed in *The Pesticide Handbook*, 12th Edition, C. D. S. Tomlin, ed., British Crop Protection Council, p. 1243 et. seq. (2000).

Members of the class of chloroacetamides (also known as chloroacetanilides) include: acetochlor (also known as 2-Chloro-N-(ethoxymethyl)-N-(2-ethyl-6-methylphenyl)acetamide); alachlor (also known as 2-Chloro-N-(2,6-diethylphenyl)-N-(methoxymethyl)acetamide); butachlor (also known as 2-chloro-2,6-diethyl-N-(butoxymethyl)-acetanilide); dimethachlor (2-chloro-N-(2,6-dimethylphenyl)-N-(2-methoxyethyl)acetamide); dimethenamide (also known as 2-chloro-N-(2,4-dimethyl-3-thienyl)-N-(2 methoxy-1-methylethyl) acetamide; metazachlor (also known as 2-chloro-N-(2,6-dimethylphenyl)-N-(2-methoxy-ethyl)acetamide); metolachlor (also known as 2-Chloro-N-(2-ethyl-6-methylphenyl)-N-(2-methoxy-1-methylphenyl)acetamide); propachlor (also known as 2-Chloro-N-isopropylacetanilide); propisochlor; and thenylchlor (also known as 2-chloro-N-(2,6-dimethylphenyl)-N-((3-methoxy-2-thienyl)methyl)acetamide).

Members of the class of imidazolinones include imazameth (also known as AC 263, 222 or ±2-(4,5-dihydro-4-methyl-4-(1-methylethyl)-5-oxo-1H-imidazol-2-yl)-5-methyl-3-pyridinecarboxylic acid); imazamethabenz-methyl (also known as a mixture of ± methyl 2-(4,5-dihydro-4-methyl-4-(1-methylethyl)-5-oxo-1H-imidazol-2-yl)-4-methylbenzoate and ± methyl 2-(4,5-dihydro-4-methyl-4-(1-methylethyl)-5-oxo-1H-imidazol-2-yl)-5-methylbenzoate in about a 3:2 ratio); imazamox (also known as ±2-(4,5-dihydro-4-methyl-4-(1-methylethyl)-5-oxo-1H-imidazol-2-yl)-5-(methoxymethyl)-3-pyridinecarboxylic acid); imazapyr (also known as 2-(4-isopropyl-4-methyl-5-oxo-2-imidazolin-2-yl); imazaquin (also known as ±2-(4,5-dihydro-4-methyl-4-(1-methylethyl)-5-oxo-1H-imidazol-2-yl)-3-quinolinecarboxylic acid); and imazethapyr (also known as ±5-Ethyl-2-(4-isopropyl-4-methyl-5-oxo-2-imidazolin-2-yl) nicotinic acid.

Members of the class of oxyacetamides include flufenacet (also known as:
N-(4-fluorophenyl)-N-(1-methylethyl)-2-[[5-(trifluoromethyl)-1,3,4-thiadiazol-2-yl]oxy]acetamide or BAY FOE 5043); and mefenacet (also known as 2-(2-benzothiazolyloxy)-N-methyl-N-phenylacetamide).

Members of the class of sulfonylureas include amidosulfuron (also known as
N-(((((4,6-dimethoxy-2-pyrimidinyl)amino)carbonyl)amino)sulfonyl)-N-methyl-methanesulfonamide);
azimsulfuron (also known as N-(((4,6-dimethoxy-2-pyrimidinyl)amino)carbonyl)-1-methyl-4-(2-methyl-2H-tetrazol-5-yl)-1H-pyrazole-5-sulfonamide);
bensulfuron-methyl (also known as 2-[[[[[(4,6-dimethoxy-2-pyrimidinyl)amino]carbonyl]amino]sulfonyl]methyl]benzoic acid methyl ester);
chlorimuron-ethyl (also known as 2-[[[[(4-chloro-6-methoxy-2-pyrimidinyl)amino]carbonyl]amino]sulfonyl] benzoic acid ethyl ester);
chlorsulfuron (also known as 2-Chloro-N-(((4-methoxy-6-methyl-1,3,5-triazin-2-yl)amino)carbonyl)benzenesulfonamide);
cinosulfuron (also known as 3-(4-6-Dimethoxy-1,3,5-triazin-2-yl)-1-[2-(2-methoxyethoxy)-phenylsulfonyl]-urea);
cyclosulfamuron (also known as N-[[[2-(cyclopropylcarbonyl)phenyl]amino]sulfonyl]-N'-(4,6-dimethoxy-2-pyrimidinyl)urea
ethametsulfuron-methyl (also known as 2-[[[[[4-ethoxy-6-(methylamino)-1,3,5-triazin-2-yl]amino]carbonyl] amino]sulfonyl]benzoic acid);
ethoxysulfuron (also known as 2-ethoxyphenyl[[(4,6-dimethoxy-2-pyrimidinyl)amino]carbonyl]sulfamate);
flazasulfuron (also known as N-[[(4,6-dimethoxy-2-pyrimidinyl)amino]carbonyl]-3-(trifluoromethyl)-2-pyridinesulfonamide);
flupyrsulfuron-methyl-sodium (also known as 2-[[[[(4,6-dimethoxy-2-pyrimidinyl)amino]carbonyl]amino]sulfonyl]-6-(trifluoromethyl)-3-pyridinecarboxylic acid, sodium salt);
foramsulfuron (also known as -[[[[(4,6-dimethoxy-2-pyrimidinyl)amino]carbonyl]amino]sulfonyl]-4-(formylamino)-N,N-dimethylbenzamide); flumetsulam (also known as 2-(2,6-difluorophenylsulphamoyl)-5-methyl [1,2,4]triazolo[1,5-a]pyrimidine;
halosulfuron-methyl (also known as 3-chloro-5-[[[[(4,6-dimethoxy-2-pyrimidinyl)amino]carbonyl]amino]sulfonyl]-1-methyl-1H-pyrazole-4-carboxylic acid);
imazosulfuron (also known as 2-chloro-N-[[(4,6-dimethoxy-2-pyrimidinyl)amino]carbonyl]imidazo[1,2-a]pyridine-3-sulfonamide);
iodosulfuron-methyl-sodium (also known as 4-iodo-2-[[[[(4-methoxy-6-methyl-1,3,5-triazin-2-yl)amino]carbonyl]amino]sulfonyl]benzoic acid, sodium salt);
mesosulfuron-methyl (also known as 2-[[[[(4,6-dimethoxy-2-pyrimidinyl)amino]carbonyl]amino]sulfonyl]-4-[[(methylsulfonyl)amino]methyl]benzoic acid, methyl ester);
mesosulfuron-methyl (also known as 2-[[[[(4-methoxy-6-methyl-1,3,5-triazin-2-yl)amino]carbonyl]amino]sulfonyl]benzoic acid, methyl ester);
nicosulfuron (also known as 2-[[[[(4,6-dimethoxy-2-pyrimidinyl)amino]carbonyl]amino]sulfonyl]-N,N-dimethyl-3-pyridinecarboxamide);
oxasulfuron (also known as 3-oxetanyl 2-[[[[(4,6-dimethyl-2-pyrimidinyl)amino]carbonyl]amino]sulfonyl]benzoate);
primisulfuron-methyl (also known as 2-[[[[[4,6-bis(difluoromethoxy)-2-pyrimidinyl]amino]carbonyl]amino]sulfonyl]benzoic acid, methyl ester);
prosulfuron (also known as N-[[(4-methoxy-6-methyl-1,3,5-triazin-2-yl)amino]carbonyl]-2-(3,3,3-trifluoropropyl)benzenesulfonamide);
pyrazosulfuron-ethyl (also known as 5-[[[[(4,6-dimethoxy-2-pyrimidinyl)amino]carbonyl]amino]sulfonyl]-1-methyl-1H-pyrazole-4-carboxylic acid, ethyl ester);

rimsulfuron (also known as N-[[(4,6-dimethoxy-2-pyrimidinyl)amino]carbonyl]-3-(ethylsulfonyl)-2-pyridinesulfonamide);

sulfometuron-methyl (also known as 2-[[[[(4,6-dimethyl-2-pyrimidinyl)amino]carbonyl]amino]sulfonyl]benzoic acid, methyl ester);

sulfosulfuron (also known as N-[[(4,6-dimethoxy-2-pyrimidinyl)amino]carbonyl]-2-(ethylsulfonyl)imidazo[1,2-α]pyridine-3-sulfonamide);

thifensulfuron-methyl (also known as 3-[[[[(4-methoxy-6-methyl-1,3,5-triazin-2-yl)amino]carbonyl]amino]sulfonyl]-2-thiophenecarboxylic acid, methyl ester);

triasulfuron (also known as -(2-chloroethoxy)-N-[[(4-methoxy-6-methyl-1,3,5-triazin-2-yl)amino]carbonyl] benzenesulfonamide);

tribenuron-methyl (also known as 2-[[[[(4-methoxy-6-methyl-1,3,5-triazin-2-yl)methylamino]carbonyl]amino] sulfonyl]benzoic acid, methyl ester); and triflusulfuron-methyl (also known as 2-[[[[[4-(dimethylamino)-6-(2,2,2-trifluoroethoxy)-1,3,5-triazin-2-yl] amino]carbonyl]amino]sulfonyl]-3-methylbenzoic acid, methyl ester).

Members of the class of triazines include atrazine (also known as 6-chloro-N-ethyl-N'-(1-methylethyl)-1,3,5-triazine-2,4-diamine); and simazine (also known as 6-chloro-N,N'-diethyl-1,3,5-triazine-2,4-diamine).

Members of the class of triazanones include hexazinone (also known as 3-cyclohexyl-6-(dimethylamino)-1-methyl-1,3,5-triazine-2,4(1H,3H)-dione); metamitron (also known as 4-amino-3-methyl-6-phenyl-1,2,4-triazin-5(4H)-one); metribuzin (also known as 4-amino-6-(1,1-dimethylethyl)-3-(methylthio)-1,2,4-triazin-5(4H)-one); and amitrole (also known as 1H-1,2,4-triazol-3-amine);

Members of the class of triketones include mesotrione (also known as 2-[4-(methylsulfonyl)-2-nitrobenzoyl]-1,3-cyclohexanedione) and sulcotrione (also known as 2-[2-chloro-4-(methylsulfonyl)benzoyl]-1,3-cyclohexanedione;

Members of the class of isoxazoles include isoxaflutole (also known as (5-cyclopropyl-4-isoxazolyl)[2-(methylsulfonyl)-4-(trifluoromethyl)phenyl]methanone).

Both monocotyledons and dicotyledons may be protected from herbicidal injury using the method of the present invention. Monocotyledons are generally preferred. Maize or corn is preferred according to the present invention.

Depending on their properties, the chloronicotinyl insectide compositions employed in accordance with the invention can be used for pretreating the seed of a crop plant (seed dressing), or be incorporated into the seed furrows prior to sowing or applied together with herbicide before or after plant emergence. The pre-emergence treatment includes not only treatment of the area under cultivation prior to sowing but treatment of the areas under cultivation where the seeds have been planted and the plants have not yet emerged. Application of the chloronicotinyl insecticide composition together with herbicide is provided. To this end, tank mixes or ready to use mixtures may be employed. The application rates of chloronicotinyl insecticide composition required may vary within wide limits depending on the crop used and the herbicidal composition used and are generally from 0.001 to 5 kg, preferably 0.005 to 0.5 kg, of chloronicotinyl insecticide per hectare.

Seed dressings or seed treatments can be accomplished by methods known to those of skill in the art For example seed may be treated by using standard operating procedures associated with known seed treaters. The Gustafson LLC/Trace Chemicals LLC manual entitled *Standard Operating Procedure Operation, Calibration and Maintenance of the Niklas Seed Treater Universal-Laboratory Batch Type W.N.*-5/01, available from Gustafson, 15012 County Road 22, McKinney Tex. 75070-6279. The insecticidal composition is applied generally at a rate of from 0.05 mg per seed to 3 mg/seed.

The method of the present invention may also be employed for controlling harmful plants in crops of genetically engineered plants that are either known or still to be developed. As a rule, transgenic plants are distinguished by particular, advantageous properties, for example by resistance to certain crop protection agents, resistance to plant diseases or pathogens causing plant diseases such as particular insects or microorganisms such as fungi, bacteria or viruses. Other particular properties relate, for example, to the harvested material in terms of quantity, quality, storing properties, composition and specific constituents. Thus, there are known transgenic plants with an increased starch content or with an altered starch quality, or those where the harvested material has a different fatty acid composition.

The present invention may be used in economically important crops, ornamental plants or transgenic crops and transgenic ornamental plants, for example cereals such as wheat, barley, rye, and oats, sorghum, millet, rice, cassava, maize, sugar beet, cotton, soya, oilseed rape, potatoes, tomatoes, peas and other vegetables.

When the combinations according to the invention are applied in transgenic crops, effects on harmful plants to be observed in other crops are frequently accompanied by effects which are specific for application in the transgenic crop in question, for example an altered or specifically widened weed spectrum which can be controlled, altered application rates which may be used, preferably good compatibility with the herbicides to which the transgenic crop is resistant, and altered growth and yield of the transgenic crop plants.

The chloronicotinyl insecticide compositions are generally applied as agrochemically acceptable formulations. Examples of possible formulations which are suitable are: wettable powders (WP), emulsifiable concentrates (EC), water-soluble powders (SP), water-soluble concentrates (SL), concentrated emulsions (BW) such as oil-in-water and water-in-oil emulsions, sprayable solutions or emulsions, capsule suspensions (CS), oil-water-based dispersions (SC), suspoemulsions, suspension concentrates, dusts (DP), oil-miscible solutions (OL), seed-treatment products, granules (GR) in form of microgranules, spray granules, coated granules and adsorption granules, granules for soil application broadcasting, water-soluble granules (SG), water-dispersible granules (WG), ULV formulations, micro-capsules and waxes. These individual formulation types are known in principle described, for example, in: Wirmacker-Küchler, "Chemische Technologie" [Chemical Technology], Volume 7, Hauser Verlag Munich, 4th Edition 1986; Wade van Valkenburg, "Pesticide Formulations", Marcel Dekker N.Y., 1973; K Martens, "Spray Drying Handbook", 3rd Edition 1979, G. Goodwin Ltd. London.

The formulation auxiliaries which may be required, such inert materials, surfactants, solvents and other additives also known and described, for example, in: Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, Y.; C. Marsden, "Solvents Guide"; 2nd Ed., Interscience, Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-Active Ethylene Oxide Adducts], Wiss. Verlagsgesell., Stuttgart 1976; Wirmacker-Küchler, "Chemische Technologie" [Chemical Technology], Volume 7, C. Hauser Verlag Munich, Edition 1986.

Based on these formulations, it is also possible to prepare combinations with other substances which act as crop protection agents, such as insecticides, acaricides, herbicides, fungicides, and also with safeners, fertilizers and/or growth regulators, for example in the form of a ready to use mixture or tank mixture. Wettable powders are preparations that are generally uniformly dispersible in water and which, comprise the chloronicotinyl insecticide and a surfactant, e.g. an ionic or a nonionic surfactants (wetting agents, dispersants). Examples of suitable additives include polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate, or else sodium oleoylmethyltaurinate, in addition to a diluent inert substance.

To prepare the wettable powders, the chloronicotinyl insecticides are ground finely, using customary apparati such as hammer mills, blower mills air-jet mills, and simultaneously or subsequently mixed with the formulation auxiliaries. Emulsifiable concentrates are prepared, for example, by dissolving the active substance in an organic solvent, such as butanol, cyclohexanone, dimethylformamide, or higher-boiling hydrocarbons such as saturated or unsaturated aliphatic hydrocarbons or alicyclic hydrocarbons, aromatics or mixtures of the organic solvents with the addition one or more ionic and/or nonionic surfactants (emulsifiers). Examples of substances which can be used emulsifiers are: calcium alkylarylsulfonates such as calcium dodecylbenzene-sulfonate, or nonionic emulsifiers such fatty acid polyglycol esters, alkylaryl polyglycol ethers, fatty alcohol polyglycol ethers, propylene oxide/ethylene oxide condensates, alkyl polyethers, sorbitan esters, for example sorbitan fatty acid esters or polyoxyethylene sorbitan esters, for example polyoxyethylene sorbitan fatty acid esters.

Dusts are generally obtained by grinding the active substance with finely distributed solid substances, for example talc, natural clays such as kaolin, bentonite and pyrophyllite, or diatomaceous earth. Suspension concentrates can be water-based or oil-based. They can be prepared, for example, by wet grinding using commercially available bead mills with or without an addition of surfactants, for example those which have already been mentioned above in the case of the other formulation types. Emulsions, for example oil-in-water emulsions (EW), can be prepared, for example, by means of stirrers, colloid mills and/or static mixers using aqueous organic solvents in the presence or absence of surfactants which have already been mentioned above, for example, in the case of the other formulation types. Granules can be prepared either by spraying the active substance onto adsorptive, granulated inert material or by applying active substance concentrates to the surface of carriers such as sand, kaolinites or granulated inert material with the aid of binders, for example polyvinyl alcohol, sodium polyacrylate or else mineral oils. Suitable active substances can also be granulated in the manner which is conventional for the preparation of fertilizer granules, if desired as a mixture with fertilizers. As a rule, water-dispersible granules are prepared by the customary processes such as Spray drying, fluidized bed granulation, disk granulation, mixing with high-speed mixers, and extrusion without solid inert material.

For the preparation of disk, fluidized-bed, extruder and spray granules see, for example, processes in "Spray-Drying Handbook" 3rd Ed. 1979, G. Goodwin Ltd., London, J. E. Browning; "Agglomeration", Chemical and Engineering 1967, pages 147 et seq., "Perry's Chemical Engineeres Handbook", 5th Ed., McGraw-Hill, New York 1973, p. 8-57. For further details on the formulation of crop protection products see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical preparations generally comprise from 0.1 to 99% by weight, in particular from 0.1 to 95% by weight, of chloronicotinyl insecticide and from 1 to 99.9% by weight, in particular 5 to 99.8% by weight of a solid or liquid additive and 0 to 25% by weight, in particular 0.1 to 25% by weight of a surfactant. In wettable powders, the active substance concentration is, for example, approximately 10 to 90% by weight, the remainder to 100% by weight being composed of customary formulation components. In the case of emulsifiable concentrates, the concentration of active substance is approximately 1 to 80% by weight. Formulations in the form of dusts comprise 1 to 20% by weight of active substance, sprayable solutions comprise approximately 0.2 to 20% by weight of active substance. In the case of granules, such as water-dispersible granules, the active substance content depends partly on whether the active compound is in liquid or solid form. The active substance content of the water-dispersible granules is, for example, between 10 and 90% by weight. Besides this, formulations of chloronicotinyl insecticides substances may comprise, if appropriate, the adhesives, wetting agents, dispersants, emulsifiers, penetrants, preservatives, antifreeze agents, solvents, fillers, carriers, colorants, antifoams, evaporation inhibitors and pH and viscosity regulators which are customary in each case.

EXAMPLES

Example 1

Growth Chamber Experiments

A. Pre-Emergent Herbicide Treatments

The following herbicides were applied at the indicated rates to soil in containers that were placed in growth chambers. One herbicide was Define® DF herbicide which contains flufenacet as an active ingredient and is available from Bayer CropScience LP, Research Triangle Park, N.C. USA. Another herbicide was Axiom® DF herbicide which is a 4:1 mixture of flufenacet and metribuzin and is available from Bayer CropScience LP. A third herbicide was Epic® DF herbicide which is a 4.8: 1 mixture of flucenacet and isoxaflutole and is available from Bayer CropScience.

Separate portions of Pioneer 33G28 hybrid corn seeds were each treated with one of the following listed insecticides according to the standard protocol *Standard Operating Procedure Operation, Calibration and Maintenance of the Niklas Seed Treater Universal-Laboratory Batch Type W.N.-5/01* One insecticide was Gaucho® insecticide, available from Bayer CropScience LP, which contains imidacloprid as the active ingredient. A second insecticide was Poncho® insecticide available from Bayer CropScience LP which contains clothianidin as the active ingredient. A third insecticide was Prescribe® insecticide available from Gustafson LLC, 1400 Preston Road, Suite 400, Piano, Tex. 75093, which contains imidacloprid as the active ingredient. A fourth insecticide was Cruiser® insecticide available from Syngenta Crop Protection, Greensboro N.C. USA which contains thiomethoxam as the active ingredient.

The seeds treated as described above were planted in small pots and the above-identified pre-emergent herbicides were applied to soil surface one day later. A control soil received no herbicide treatment. One group of pots contained seeds that were untreated with insecticide and which received herbicidal treatment. All pots were maintained in controlled-environment growth chambers set at 60° F. night and 80° F. day (12-hour photoperiod) for 6 days until most seedlings had emerged. Settings on the growth chambers were then changed to cold, wet conditions (50° F. day, 40° F. night, 12-hour photoperiod, 85% Relative.Humidity.) for the next 10 days to simulate normal cold, moist field conditions of the spring. These conditions commonly can stress young seedlings and increase phytotoxic response of seedlings to herbicides. Evaluations of the crop response were made at 6, 16, and 22 days after herbicide application. Those plants emerging from treated seeds showed generally less phytotoxicity than plants emerging from untreated seeds. Typically, damaged plants visually showed more stunting, less vigorous growth, fewer tillers, yellowing and other recognizable signs of phytotoxicity.

B. Post-Emergent Herbicide Treatments

In another growth chamber experiment, separate portions of Pioneer 33G28 hybrid corn seed were treated as described above and planted in small pots as above. All pots were maintained in controlled-environment growth chambers set at 60° F. night and 80° F. day (12-hour photoperiod) for 8 days until most seedlings had emerged. Settings on the growth chambers were then changed to cold, wet conditions (50° F. day, 40° F. night, 12-hour photoperiod, 85% Relative.Humidity.) for the next 8 days to simulate normal cold, moist field conditions of the spring, and then returned to their original settings (60° F. night, 80° F. day).

These corn plants were sprayed 3 days later, at the 2-leaf stage (e.g. post-emergence treatment), with the following identified herbicides. One was Option® herbicide available from Bayer CropScience LP having foramsulfuron as the active ingredient along with the safener isoxadifen. The second was Callisto® herbicide available from Syngenta CropProtection, Greensboro, N.C., USA having mesotrione as the active ingredient. A control soil received no herbicide treatment. Some seeds were not treated but were treated with herbicides. Evaluations of the crop response were made at 7 and 11 days after herbicide application. Those plants emerging from treated seeds showed generally less phytotoxicity than plants emerging from untreated seeds. Those plants emerging from treated seeds showed generally less phytotoxicity than plants emerging from untreated seeds. Typically, damaged plants visually showed more stunting, less vigorous growth, fewer tillers, yellowing and other recognizable signs of phytotoxicity.

Example 2

Field Experiments

A. Pre-Emergent Herbicide Treatments

Corn seeds from several commercial hybrids were treated with the following listed insecticides according to the standard protocol Standard Operating Procedure Operation, Calibration and Maintenance of the Niklas Seed Treater Universal-Laboratory Batch Type W.N.-5/01. These were Gaucho® insecticide and Poncho® insecticide available from Bayer CropScience LP); Prescribe® insecticide available from Gustafson (Gustafson LLC, 1400 Preston Road, Suite 400, Piano, Tex. 75093, phone number 1-800-368-6130); and Cruiser® insecticide available from Syngenta Crop Protection, Greensboro N.C. USA. Gaucho® insecticide contains imidacloprid as the active ingredient, Poncho® insecticide contains clothianidin as the active ingredient, Prescribe® insecticide contains imidacloprid as the active ingredient and Cruiser® insecticide contains thiomethoxam as the active ingredient.

The insecticide-treated seeds were planted into field plots at three locations and several commercial herbicide treatments were applied to the soil surface and compared to control treatments (no herbicide treatment). Soil applied herbicide treatments included registered products used at recommended commercial rates selected for the soil characteristics, and treatments at 3 times the commercial rates and included: Define® herbicide (flufenacet), Axiom® herbicide (a 4:1 mixture of flufenacet and metribuzin) or Epic® herbicide (a 4.8:1 mixture of flufenacet plus isoxaflutole). All soil-applied herbicides used are available from Bayer CropScience LP, Research Triangle Park, N.C. USA. Multiple evaluations of the crop response were made between 2 and 9 weeks after application.

Those plants emerging from treated seeds showed generally less phytotoxicity than plants emerging from untreated seeds. Cruiser® insecticide and Poncho® insecticide generally showed exceptional results.

Those plants emerging from treated seeds showed generally less phytotoxicity than plants emerging from untreated seeds. Typically, damaged plants visually showed more stunting, less vigorous growth, fewer tillers, yellowing and other recognizable signs of phytotoxicity.

B. Post-Emergent Herbicide Treatments

In another field experiment conducted at three locations, corn seeds from several commercial hybrids were treated as described above. The insecticide-treated seeds were planted into field plots and corn plants from the planted seeds were grown to the third to fourth leaf stages. Several commercial herbicide treatments were then applied according to their labels over the corn plants in the various field plots and compared to control treatments (no herbicide treatment). The corn plants were treated with registered herbicide products at recommended commercial rates, and also with treatments at 3 times the commercial rates and included: Option® herbicide (a 1:1 mixture of foramsulfuron and the safener isoxadifen) or Callisto® herbicide (mesotrione). Option® herbicide is available from Bayer CropScience LP, Research Triangle Park, N.C. USA and Callisto® herbicide is available from Syngenta CropProtection, Greensboro N.C. USA. Evaluations of the crop response were made from approximately 1 to 7 weeks after treatment.

Those plants emerging from treated seeds showed generally less phytotoxicity than plants emerging from untreated seeds. Those plants emerging from treated seeds showed generally less phytotoxicity than plants emerging from untreated seeds. Cruiser® insecticide and Poncho® insecticide generally showed exceptional results.

C. Comparisons of Poncho® Insecticide-Treated Seed to In-furrow Insecticides Followed by Herbicide Treatments A field having four rows was planted as follows.

In a first row were planted a portion of Golden Harvest EX09385 LL hybrid corn seeds which were treated with Poncho® insecticide according to the standard protocol Standard Operating Procedure Operation, Calibration and Maintenance of the Niklas Seed Treater Universal-Laboratory Batch Type W.N.-5/0 1.

Poncho® insecticide is available from Bayer CropScience LP. Poncho® insecticide contains clothianidin as the active ingredient.

In a second row, a portion of the same Golden Harvest seeds but which had not been treated with an insecticide were planted.

In a third row, a portion of Golden Harvest seeds were planted which had been treated with in-furrow Aztec® insecticide available from Bayer CropScience (a mixture of tebupirimphos and cyfluthrin as the active ingredients).

In the fourth row, a portion of Golden Harvest seeds were planted which had been treated with in furrow Counter® insecticide availabe from BASF AG of Research Triangle Park, N.C., (active ingredient terbufos).

Several herbicide treatments were applied to the soil surface and/or over the top of the emerged corn plants compared to control treatments). Herbicide treatments at recommended rates and with recommended adjuvants included one or more of the following: Define® herbicide (flufenacet as the active ingredient), Basis Gold® herbicide (a 1:1:64.8 mixture of nicosulfuron, rimsulfuron and atrazine as the active ingredient), Option® herbicide (a 1:1 mixture of foramsulfuron as the active ingredient and the safener isoxadifen), Callisto® herbicide (mesotrione), Epic® herbicide (a 4.8:1 mixture of flufenacet plus isoxaflutole), and Equip® herbicide (in this case a 30:1:30 mixture of foramsulfuron, iodosulfuron and the safener isoxadifen). Define® herbicide, Option® herbicide, Epic® herbicide, and Equip® herbicide are from Bayer CropScience LP, Research Triangle Park, N.C. USA, Callisto® herbicide is available from Syngenta CropProtection, Greensboro N.C. USA, and Basis Gold® herbicide is available from E.I. DuPont de Nemours and Company, Crop protection, Wilmington, Del. 19898. Crop response was evaluated at 2 weeks after application. In particular, plants emerging from seeds treated with Poncho® insecticide (clothianidin) generally displayed less visual phytotoxicity than those seeds treated with in furrow insecticides.

D. Field Demonstration of Gaucho Treated Seed Followed by an Epic Herbicide Treatment Hybrid corn seeds were commercially treated with Gaucho® insecticide available from Bayer CropScience LP. Gaucho® insecticide contains imidacloprid as the active ingredient.

The insecticide-treated seeds were planted through six rows of a twelve-row planter in a field. The other six planter rows included corn seed with no insecticide treatment. The entire field was treated with a commercial application to the soil surface of Epic® herbicide (a 4.8:1 mixture of flufenacet plus isoxaflutole) at recommended rates. Epic® herbicide is available from Bayer CropScience LP, Research Triangle Park, N.C. USA. In the six rows of untreated seeds, more plant stunting and chlorotic/necrotic leaves were visually observed than in the six rows of plants emerging from treated seeds.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims that follow.

What is claimed is:

1. A method of minimizing injury to corn caused by an herbicide treatment of the corn, comprising
    (a) applying to the seed of the corn a seed treatment comprising one or more chloronicotinyl insecticides and
    (b) applying subsequently to the corn, its locus, or combinations thereof, a herbicide selected from the group consisting of chloroacetamides, imidazolinones, oxyacetamides, sulfonylureas, triazines, triketones, isoxazoles, and combinations thereof,
    wherein said insecticide operates to reduce or eliminate injury to the corn that would have otherwise occurred when the corn or its locus was subsequently treated with the herbicide.

2. The method according to claim 1, wherein the chloronicotinyl insecticide is selected from the group consisting of

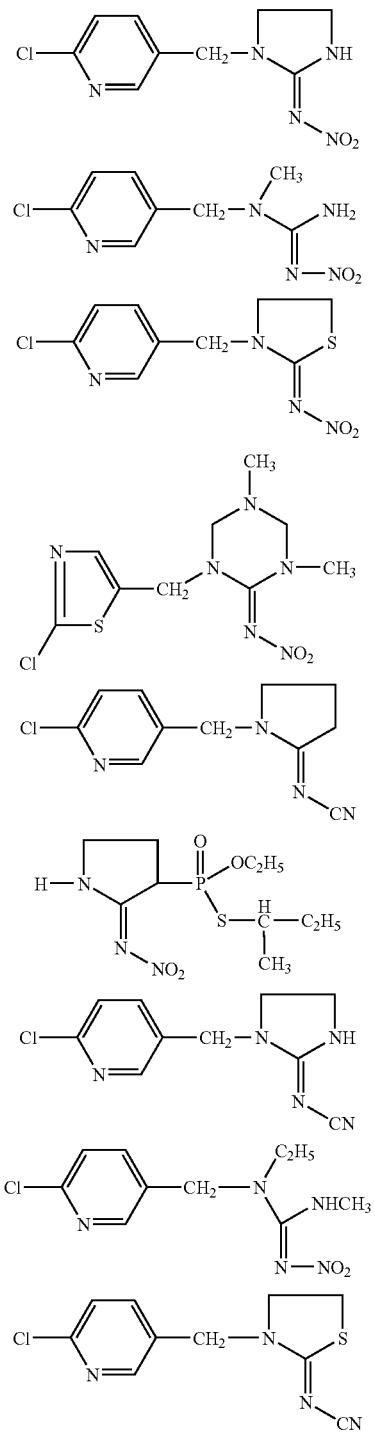

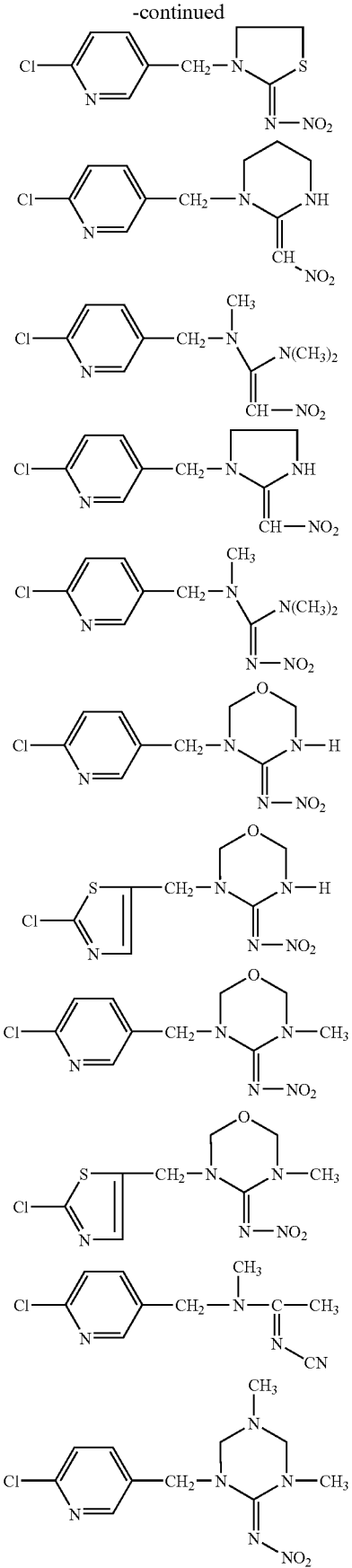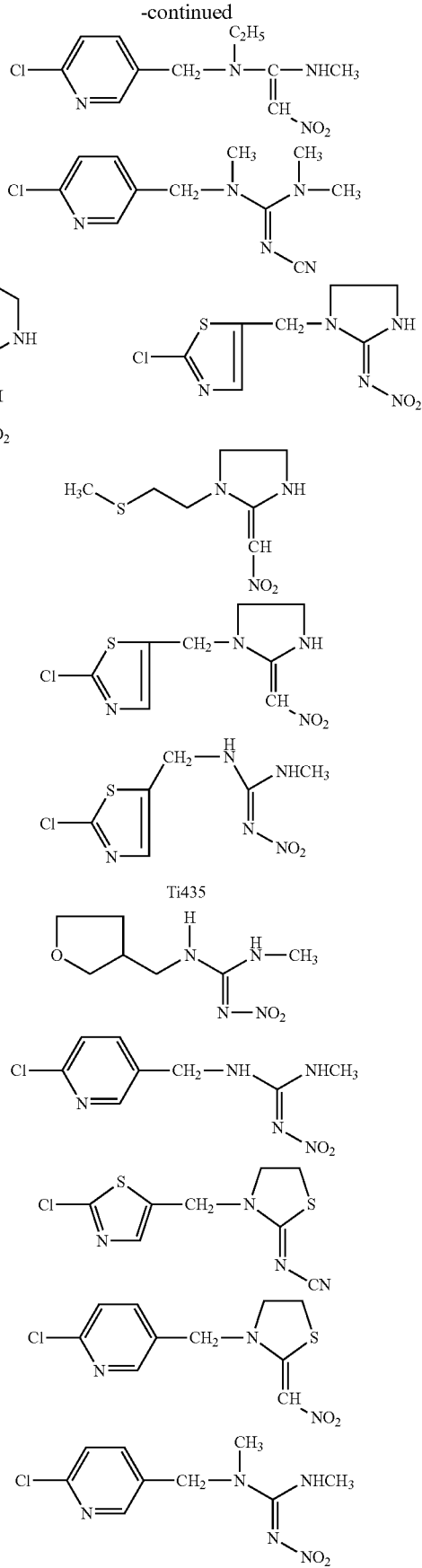

-continued

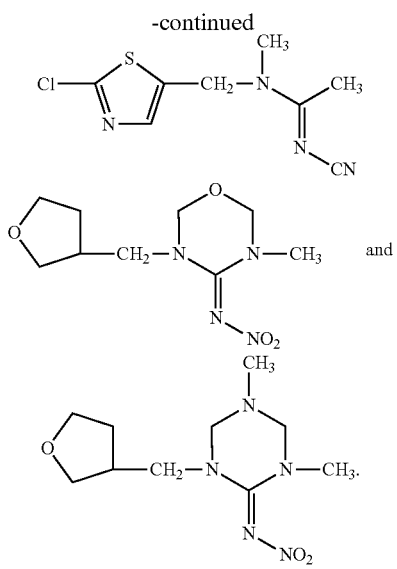

and

3. The method according to claim 1, wherein the herbicide treatment is applied as a pre-emergent treatment.

4. The method according to claim 3, wherein the herbicide treatment is applied at least one day after the insecticide treatment.

5. The method according to claim 1, wherein the herbicide treatment is applied as a post-emergent treatment.

6. The method according to claim 5, wherein the herbicide treatment is applied between a 2- and 5-leaf stage.

7. The method according to claim 5, wherein the herbicide treatment is applied at least three days after the insecticide treatment.

8. The method according to claim 1, wherein the chloronicotinyl insecticide is applied to the seed at a rate of from 0.05 mg/seed to 3 mg/seed or wherein the soil temperature at the locus of the corn at or before the time of application of the herbicide is from about 4° C. to about 25° C.

9. The method according claim 1, wherein the herbicide is applied to the soil at the locus of the corn.

10. The method according to claim 1, wherein the herbicide is applied to the foliage of the corn.

11. The method according to claim 1, wherein the seed treatment consists essentially of one or more chloronicotinyl insecticides.

12. The method according to claim 1, wherein the chloronicotinyl insecticide is imidacloprid.

13. The method according to claim 1, wherein the chloronicotinyl insecticide is clothianidin.

14. The method according to claim 1, wherein the chloronicotinyl insecticide is thiomethoxam.

15. The method according to claim 1, wherein the herbicide is flufenacet, foramsulfuron, mesotrione, metribuzin, isoxaflutole, iodosulfuron, nicosulfuron, rimsulfuron, atrazine, or combinations thereof.

16. The method according to claim 1, wherein the herbicide is imidazolinone.

17. The method according to claim 1, wherein the herbicide is oxyacetamide.

18. The method according to claim 1, wherein the herbicide is sulfonylurea.

19. The method according to claim 1, wherein the herbicide is triketone.

20. The method according to claim 1, wherein the herbicide is isoxazole.

21. The method according to claim 1, wherein the herbicide is triazine.

22. The method according to claim 1, wherein the herbicide is chloroacetamide.

23. The method according to claim 8, wherein said soil temperature at the locus of the corn at or before the time of application of the herbicide is from about 10° C. to about 20° C.

* * * * *